(12) United States Patent
Sato (10) Patent No.: US 12,082,822 B2
(45) Date of Patent: Sep. 10, 2024

(54) OPENABLE AND CLOSABLE CLIP (71) Applicant: NATIONAL UNIVERSITY CORPORATION KOCHI UNIVERSITY, Kochi (JP)

(72) Inventor: Takayuki Sato, Kochi (JP)

(73) Assignee: NATIONAL UNIVERSITY CORPORATION KOCHI UNIVERSITY, Kochi (JP)

( * ) Notice: Subject to any disclaimer, the term of this patent is extended or adjusted under 35 U.S.C. 154(b) by 528 days.

(21) Appl. No.: 17/421,827

(22) PCT Filed: Jun. 30, 2020

(86) PCT No.: PCT/JP2020/025641
§ 371 (c)(1),
(2) Date: Jul. 9, 2021

(87) PCT Pub. No.: WO2021/033431
PCT Pub. Date: Feb. 25, 2021

(65) Prior Publication Data
US 2022/0096088 A1 Mar. 31, 2022

(30) Foreign Application Priority Data
Aug. 19, 2019 (JP) ................................ 2019-149947

(51) Int. Cl.
*A61B 17/122* (2006.01)
*A61B 17/12* (2006.01)
*A61B 90/00* (2016.01)

(52) U.S. Cl.
CPC .. *A61B 17/122* (2013.01); *A61B 2017/12004* (2013.01); *A61B 2090/3991* (2016.02)

(58) Field of Classification Search
CPC ........ A61B 17/122; A61B 2017/12004; A61B 2090/3991; A61B 17/083;
(Continued)

(56) References Cited

U.S. PATENT DOCUMENTS 5,312,426 A * 5/1994 Segawa ............... A61B 17/1227
606/157
5,520,701 A * 5/1996 Lerch ................... A61B 17/122
606/151
(Continued)

FOREIGN PATENT DOCUMENTS

CN 101933835 A 1/2011
JP 4388324 B2 12/2009
(Continued)

OTHER PUBLICATIONS

"Catalogue of Sugita Titanium Clip". Mizuho Corporation, URL: <http://www.mizuho.co.jp/pnet/neurosurgery/upload/f5a66fbd8480ed47010717423dbffa40_1.pdf>.
(Continued)

*Primary Examiner* — Tan-Uyen T Ho
*Assistant Examiner* — Osama Nemer
(74) *Attorney, Agent, or Firm* — Oliff PLC (57) ABSTRACT

An openable and closable clip for medical use includes a resin clip body, and a fastening ring to be fitted onto the clip body. Clip body includes a pair of opposing arm parts, and connecting part that connects base ends of respective arm parts. Each arm part includes curved part on a base end side, holding part on distal end side, and intermediate part between curved and holding parts. Curved part is curved in arc shape, and intermediate part has a thickness greater than that of curved part. Clip body closes in state where fastening ring is fitted onto clip body on side closer to connecting part than curved part, opens when fastening ring slides onto curved part from connecting part, and closes when fastening ring slides onto intermediate part from curved part. Openable and closable clip can be used in endoscope clip device and opens and closes stably.

6 Claims, 10 Drawing Sheets

(58) Field of Classification Search
CPC .... A61B 2090/3941; A61B 2090/3966; A61B 90/39; A61B 17/12; A61B 2017/00584; A61B 17/0487; A61B 17/22
See application file for complete search history.

(56) References Cited

U.S. PATENT DOCUMENTS

| | | | | |
|---|---|---|---|---|
| 5,634,932 | A | * | 6/1997 | Schmidt ............... A61B 17/122 606/142 |
| 5,733,295 | A | | 3/1998 | Back et al. |
| 6,251,117 | B1 | * | 6/2001 | Kringel ............... A61B 17/1227 606/158 |
| 6,991,634 | B2 | * | 1/2006 | Sugiyama ............ A61B 17/122 606/151 |
| 9,572,579 | B2 | * | 2/2017 | Weisshaupt ............. B29C 45/73 |
| 11,311,299 | B2 | * | 4/2022 | Sauter ................ A61B 17/1227 |
| 2010/0331674 | A1 | * | 12/2010 | Sohn .................. A61B 17/1227 600/431 |
| 2012/0184976 | A1 | * | 7/2012 | Nakamura ........... A61B 17/122 606/158 |
| 2013/0072946 | A1 | | 3/2013 | Terada |
| 2018/0333156 | A1 | * | 11/2018 | Hayashi ............. A61B 17/1285 |
| 2019/0231352 | A1 | * | 8/2019 | Maekubo ............. A61B 17/122 |
| 2021/0106335 | A1 | * | 4/2021 | Sugitani ............... A61B 17/122 |

FOREIGN PATENT DOCUMENTS

| | | | |
|---|---|---|---|
| JP | 3157486 U | 2/2010 | |
| JP | 2011-005227 A | 1/2011 | |
| JP | 2011-162445 A | 8/2011 | |
| JP | 5045484 B2 | 10/2012 | |
| JP | 5134102 B2 | 1/2013 | |
| JP | 2013-063109 A | 4/2013 | |
| JP | 2017-192513 A | 10/2017 | |
| JP | 6294016 B2 | 3/2018 | |
| WO | WO-0108568 A1 * | 2/2001 | ......... A61B 17/1227 |
| WO | WO-02096303 A1 * | 12/2002 | ......... A61B 17/0643 |
| WO | 2016/132596 A1 | 8/2016 | |
| WO | 2016/157565 A1 | 10/2016 | |

OTHER PUBLICATIONS

Sep. 15, 2020 International Search Report issued in International Patent Application No. PCT/JP2020/025641.
Jan. 4, 2024 Office Action issued in Chinese Patent Application No. 202080015803.8.

* cited by examiner

(SIDE VIEW AS VIEWD IN DIRECTION A)

FIG. 1D

(SIDE VIEW AS VIEWD IN DIRECTION B)

FIG. 1E

(SIDE VIEW AS VIEWD IN DIRECTION C)

FIG. 1F (CROSS-SECTIONAL VIEW TAKEN ALONG LINE x-x)

FIG. 5B (SIDE VIEW AS VIEWD IN DIRECTION A)

OPENABLE AND CLOSABLE CLIP

TECHNICAL FIELD

The present invention relates to an openable and closable clip for medical use.

BACKGROUND ART

As a hemostatic clip or a marker clip for identifying the position of an affected area at the time of surgery, conventionally, a clip used by attaching it to an endoscope clip device has been employed. For example, a clip including a clip body formed by bending a flat spring made of a metal such as stainless steel into a dogleg shape (Japanese character "<" shape), and a fastening ring fitted onto the clip body so as to close the clip body (Patent Literature 1), and a clip with a clip body which consists of a pair of steel arms with an outwardly arched portion and an inwardly arched portion, that can be opened and then closed by making the clip body, which has been opened, pass through a tubular sleeve (Patent Literature 2) have been known.

The Sugita clip has been used as an aneurysm clip, and is configured in such a manner that one end of the clip is formed as a coil spring, and the opposing metal arm parts extending from the coil spring cross each other, so that the clip can be opened by reducing the distance between the pair of arm parts on the coil spring side by compression.

A resin clip has been known as a surgical clip to be opened and closed directly by pinching the clip by hand, and is configured in such a manner that the ends of one side of a pair of opposing arm parts are made continuous with each other via a curved part and with the pair of arm parts crossing each other, so that the other ends of the arm parts can be opened and closed (Patent Literature 3).

CITATION LIST

Patent Literature

Patent Literature 1: Japanese Patent No. 6294016
Patent Literature 2: Japanese Patent No. 5134102
Patent Literature 3: Japanese Utility Model Registration No. 3157486

SUMMARY OF INVENTION

Technical Problem

SUMMARY OF INVENTION

Technical Problem

As a method of using the clips described in Patent Literatures 1 and 2, for example, an affected area on the mucosal surface of the digestive canal is marked before surgery using the clip described in Patent Literature 1 or 2, the digestive canal is palpated from the serous membrane surface of the digestive canal at the time of the surgery to confirm the position of the clip, that is, the position of the affected area, and then the affected area is cut off using an auto-suturing device called a stapler (e.g., Endo GIA Tri-Staple (registered trademark) or Endo GIA Ultra Universal Stapler (registered trademark) manufactured by COVIDIEN JAPAN INC.). If the place to cut, that is, if the cut line is situated near the clip, however, the stapler may bite the clip. Since the clip is made of metal, the clip will not fracture, thereby disadvantageously stopping the movement of the stapler.

In view of this, a clip made of a resin can be considered, so as to allow the clip to fracture when the stapler bites the clip. According to the clip described in Patent Literature 1, however, the clip body is formed by bending the metal flat spring into a dogleg shape. Once the arm parts of the clip body are fastened by the fastening ring, the arm parts attempt to open due to the nature of elasticity seeking to resume their original shape, thereby generating a strong frictional force between the fastening ring and the arm parts. Thus, this clip has a structure which does not allow the fastening ring to be easily removed from the arm parts. Therefore, it is considered that the clip described in Patent Literature 1 needs to employ a material with considerably high elasticity. The flexural modulus of resin is about one-hundredth of the flexural modulus of metal. In addition to this, resin has a narrow range of elastic deformation. It is therefore considered that resin is inappropriate as a material of the clip described in Patent Literature 1. That is, if the clip having the shape described in Patent Literature 1 is formed of a resin, the clip body is plastically deformed too easily when the fastening ring is fitted onto the clip body to close the clip body. Thus, the fastening ring cannot be kept on the arm parts by creating a strong enough frictional force between the fastening ring and the arm parts as in the case where the clip is made of metal, and the clip body cannot maintain its closed state.

The shape of the clip body including the outwardly arched portion and the inwardly arched portion, described in Patent Literature 2, is premised on being formed by a metal flat spring. Thus, if the clip body having this shape is formed of a resin, which has a flexural strength lower than that of metal, the clip body may break when passed through the tubular sleeve so as to be opened and closed.

The clip described in Patent Literature 3 is made of a resin. In a case where a clip has a shape created by crossing a pair of arm parts, as in the clip described in Patent Literature 3 and Sugita clip, however, distortion occurs when the pair of opposing arm parts are compressed to open the clip. Such distortion makes it difficult to achieve stable opening and closing of the clip. In particular, if the clip is produced in a size that allows the clip to pass through a sheath of an endoscope clip device so as to be used in that device, the opening and closing operations become unstable.

In view of this, it is an object of the present invention to provide a resin clip for medical use, which can be used also in an endoscope clip device, capable of opening and closing stably.

Solution to Problem

The present inventor has arrived at the present invention upon conceiving that: in order to stabilize a state holding a body tissue in a clip including a clip body and a fastening ring, configuring the clip so that the clip body is closed with no fastening ring being fitted thereon, the clip body is opened by fitting the fastening ring onto one end of the clip body and causing the fastening ring to slide toward the other end side, and the clip body is closed by causing the fastening ring to further slide toward the other end side is effective; and in order to enable a resin clip to perform such opening and closing operations, the clip body only has to have a particular shape.

That is, the present invention is an openable and closable clip for medical use, comprising a clip body made of a resin, and a fastening ring to be fitted onto the clip body, wherein
the clip body includes a pair of opposing arm parts, and a connecting part that connects base ends of the respective arm parts,
each of the arm parts includes a curved part on a base end side, a holding part on a distal end side, and an intermediate part between the curved part and the holding part,
the curved part is curved in an arc shape so that the pair of arm parts are away from each other,
the intermediate part has a thickness greater than that of the curved part, and
configuring an inner diameter of the fastening ring to be greater than a maximum diameter of the connecting part, lesser than a maximum distance between outer surfaces of the pair of curved parts in a closed state of the clip body, and greater than a distance between outer surfaces of curved part-side regions of the pair of intermediate parts in the closed state of the clip body enables the clip body to close when the fastening ring is removed from the clip body and when the fastening ring is fitted onto the clip body on a side closer to the connecting part than the curved part, open when the fastening ring slides onto the curved part from the connecting part, and close when the fastening ring slides onto the intermediate part from the curved part.

Advantageous Effects of Invention

According to the openable and closable clip of the present invention, the clip body is made of a resin. This allows the openable and closable clip to be cut even when a stapler bites the openable and closable clip at the time of surgery. Thus, the use of the stapler can be continued.

The fastening ring is kept on the intermediate parts between the curved parts and the holding parts while the openable and closable clip of the present invention is holding a body tissue. This can eliminate the possibility that the clip is detached from the affected area by the coming off of the fastening ring.

In addition, since the shape of the openable and closable clip according to the present invention can be integrally molded by a resin injection molding, the openable and closable clip can be produced at a low cost.

DESCRIPTION OF EMBODIMENTS

The present invention will be described below in detail with reference to the drawings. Note that the same reference numerals denote the identical or equivalent elements throughout the drawings.

Figure 1A:
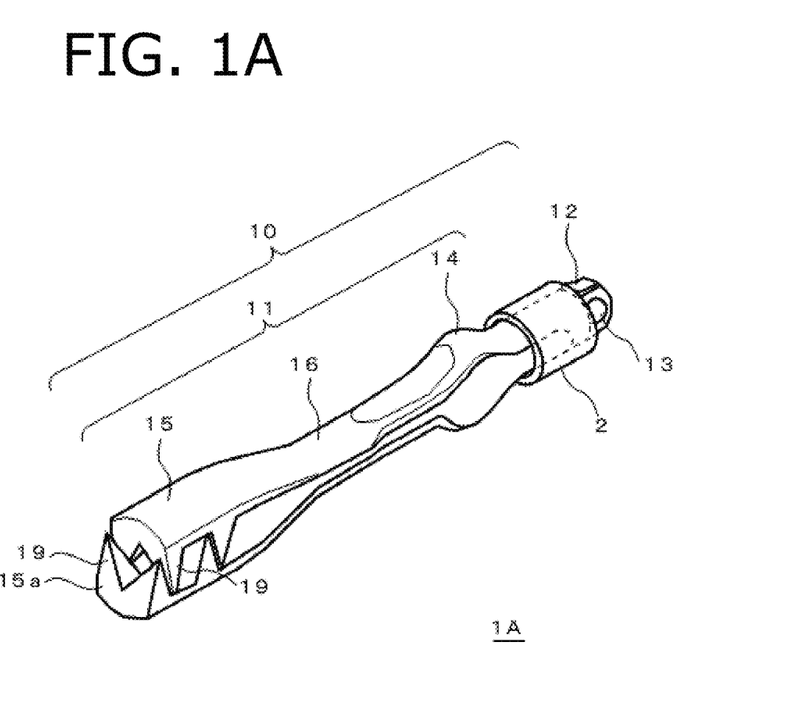
FIG. 1A is a perspective view showing an openable and closable clip according to an embodiment with a fastening ring being fitted onto a connecting part of a clip body.
Figure 2A:
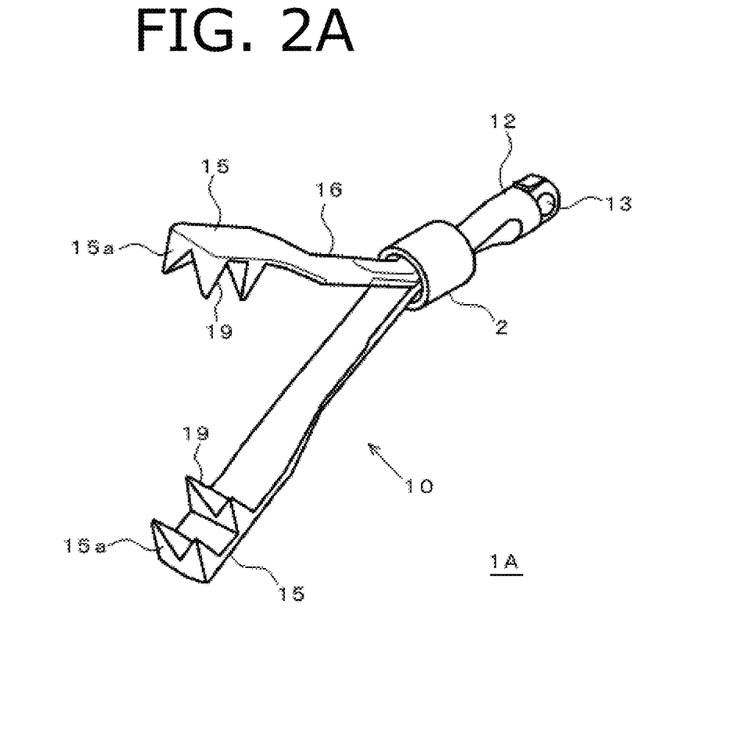
FIG. 2A is a perspective view showing the openable and closable clip according to the embodiment with the fastening ring sliding onto the curved parts.
Figure 2B:
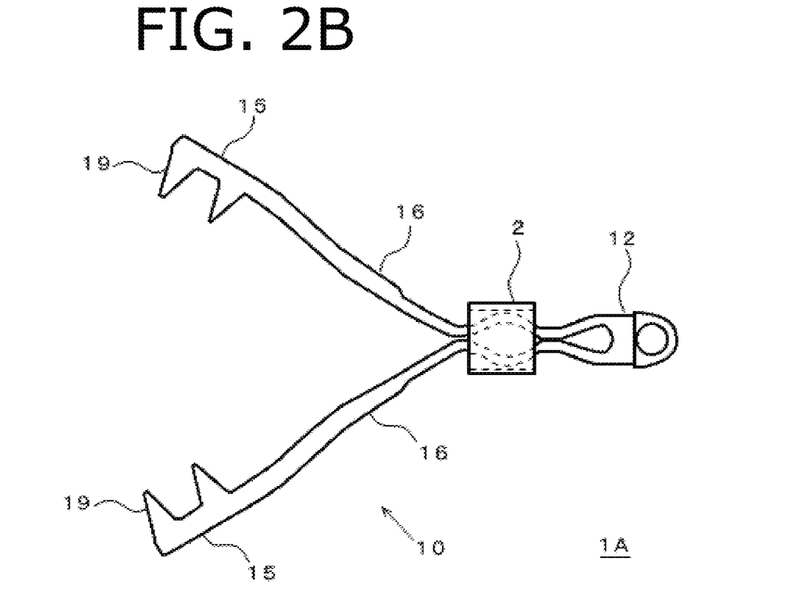
FIG. 2B is a side view showing the openable and closable clip according to the embodiment with the fastening ring sliding onto the curved parts.
Figure 3A:
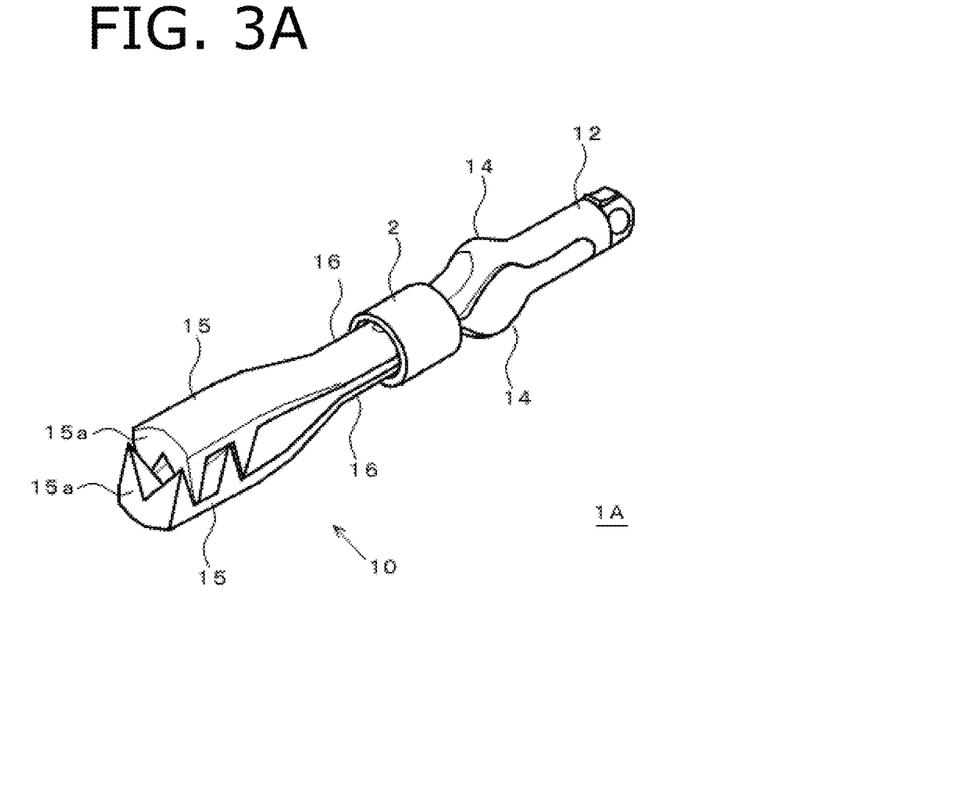
FIG. 3A is a perspective view showing the openable and closable clip according to the embodiment with the fastening ring sliding onto the intermediate part.
Figure 3B:
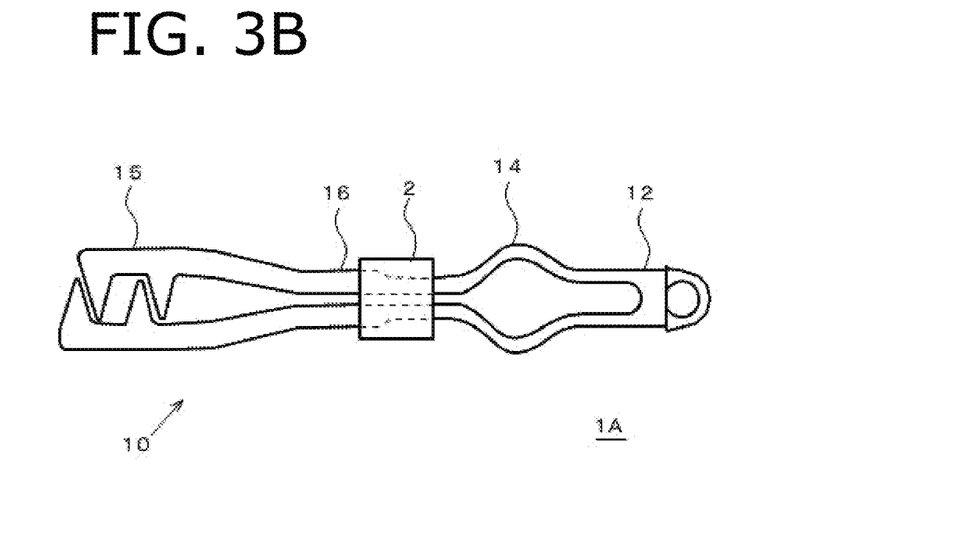
FIG. 3B is a side view showing the openable and closable clip according to the embodiment with the fastening ring sliding onto the intermediate part.

Shapes:

An openable and closable clip according to the present invention includes a clip body made of a resin, and a fastening ring made of a resin to be removably fitted onto the clip body. FIG. 1A is a perspective view showing an openable and closable clip 1A according to an embodiment of the present invention with a fastening ring 2 being fitted onto a connecting part of a clip body 10. FIG. 2A is a perspective view showing a state in which the fastening ring 2 slides onto curved parts of the clip body 10. FIG. 3A is a perspective view showing a state in which the fastening ring 2 slides onto intermediate parts of the clip body 10.

As shown in these figures, the clip body 10 includes a pair of arm parts 11 and a connecting part 12 that connects base ends of the respective arm parts 11. The openable and closable clip 1A of the present embodiment is used with the clip being attached to an endoscope clip device as will be described later. A hole 13 to be engaged with a distal end hook of a manipulation wire of the endoscope clip device is thus formed in the connecting part 12. Note that the hole 13 is provided as necessary in the present invention.

The arm part 11 of the clip body 10 has a curved part 14 on a base end side, a holding part 15 for holding an object to be clipped on a distal end side, and an intermediate part 16 between the curved part 14 and the holding part 15.

Figure 1B:
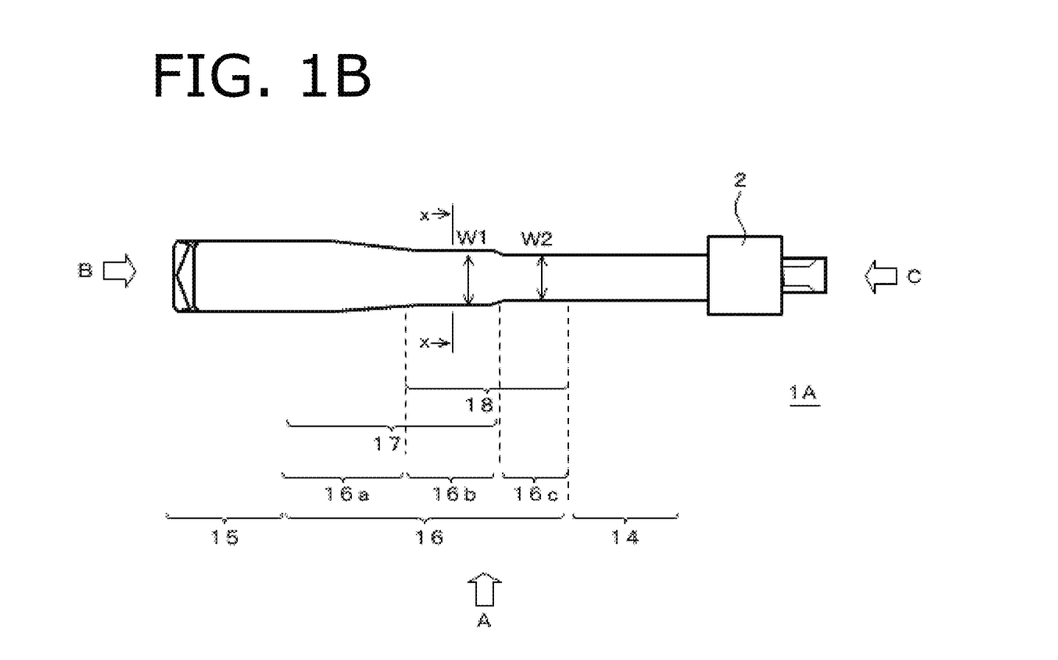
FIG. 1B is a plan view showing the openable and closable clip according to the embodiment with the fastening ring being fitted not onto curved parts but onto the connecting part.
Figure 1C:
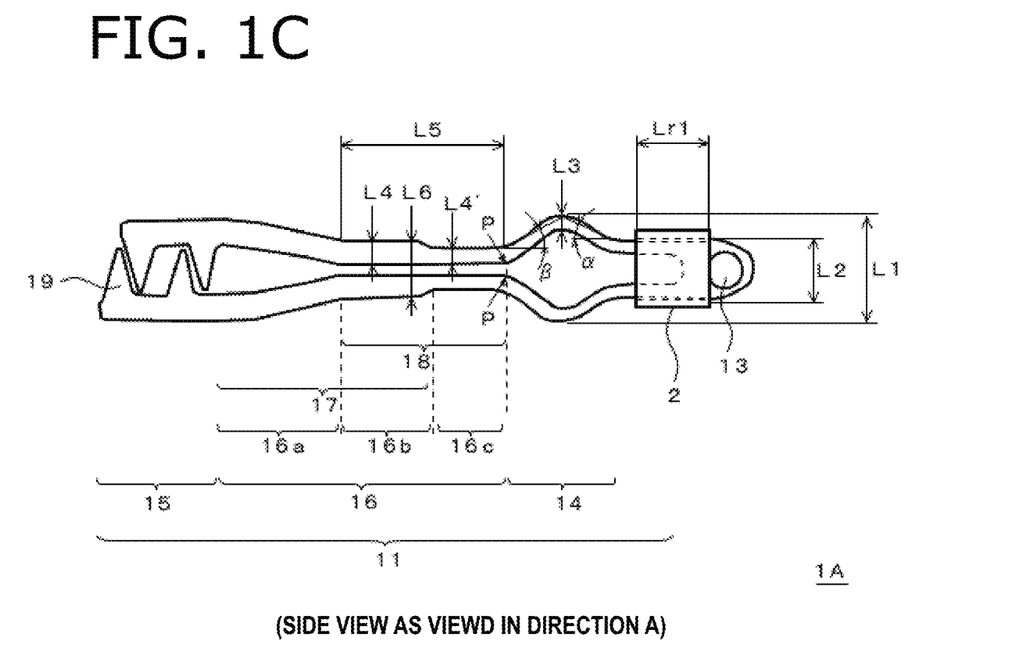
FIG. 1C is a side view of the openable and closable clip according to the embodiment as viewed in a direction A with the fastening ring being fitted not onto the curved parts but onto the connecting part.
Figure 1D:
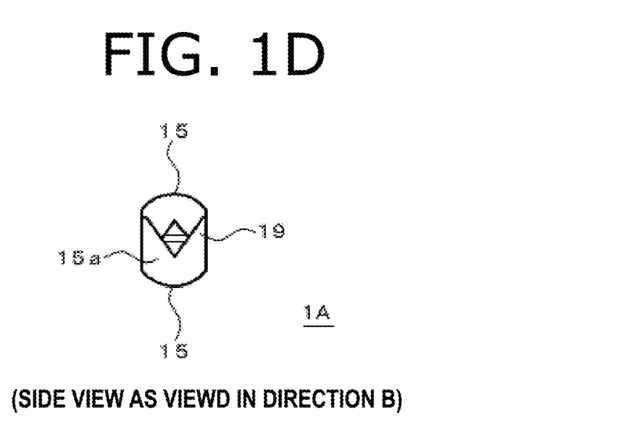
FIG. 1D is a side view of the openable and closable clip according to the embodiment as viewed in a direction B with the fastening ring being fitted not onto the curved parts but onto the connecting part.
Figure 1E:
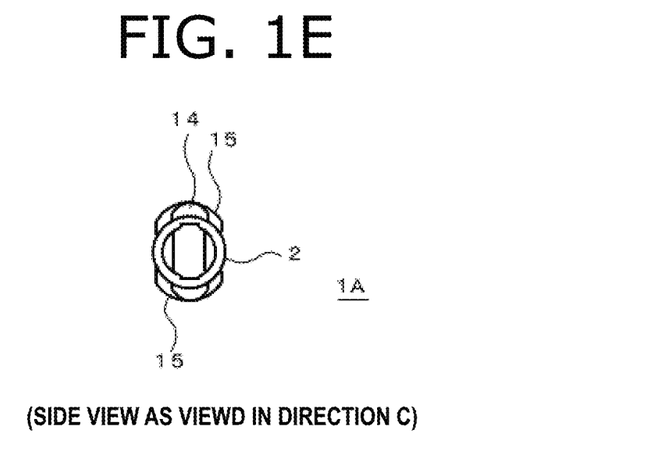
FIG. 1E is a side view of the openable and closable clip according to the embodiment as viewed in a direction C with the fastening ring being fitted not onto the curved parts but onto the connecting part.

The curved parts 14 of the pair of arm parts 11 are curved in an arc shape so as to be away from each other when the clip body 10 is closed. More specifically, the side where the surfaces of the pair of arm parts 11 oppose each other is defined as an inner side, whereas the side opposite to the opposing surfaces is defined as an outer side, the curved part 14 has a plate shape curved in a convex manner toward the outer side. A maximum distance L1 between the outer surfaces of the pair of curved parts 14 when the clip body 10 is closed is greater than an inner diameter L2 of the fastening ring 2. The value of L1/L2 is preferably less than or equal to 2, more preferably 1.7 to 1.9 (FIG. 1C). If this ratio is too large, depending on the flexural property of the resin that forms the clip body, the curved part 14 may plastically deform or break, thus making the clip body unopenable even when the fastening ring 2 slides onto the curved parts 14.

The curved part 14 has a substantially constant thickness and a shape created by making a flat plate curved in order to enable the curved part 14 to exhibit a flexural property as with a flat spring. Configuring the part to have a shape created by making a flat plate curved in a convex manner toward the outer side enables the clip body 10 on a side closer to the holding part 15 to be opened by pressing the curved shape so as to be deformed flat, and enables the deformed shape to return to its original curved shape by removing the pressing force. For the application of the endoscope clip in the present embodiment, the specific numerical value of a thickness L3 of the curved part 14 can be determined depending on the inner diameter of an outer sheath of the clip device or the length of the clip body 10. When the inner diameter of the outer sheath of the endoscope clip device is 2.1 mm, for example, the thickness L3 of the curved part 14 in the side view of the clip body 10 is preferably set to 0.2 to 0.3 mm (FIG. 1C).

As to the degree of curvature of the curved part 14, a projection angle $\alpha$ of the curved part 14 with respect to the connecting part 12 in the side view of the clip body 10 (an angle between a line connecting an end of the curved part 14 closer to the connecting part and an apex of the convex shape of the curved part 14, and the long-side direction of the arm part 11), and a projection angle $\beta$ of the curved part 14 from the intermediate part 16 (an angle between a line connecting an end of the curved part 14 closer to the intermediate part and the apex of the convex shape of the curved part 14, and the long-side direction of the arm part 11) are preferably set to be $\alpha<\beta$. For example, the projection angle $\alpha$ is preferably set to 19 to 22°, and the projection angle $\beta$ is preferably set to 23 to 26° (FIG. 1C). If these angles are too large, depending on the flexural property of the resin that forms the clip body, the curved part may plastically deform or break, thus making the clip body unopenable even when the fastening ring 2 slides onto the curved parts 14. If these angles are too small, the clip body itself cannot open widely, thus failing to hold the object to be clipped. Moreover, setting these angles to be $\alpha<\beta$ facilitates deformation of the curved part 14 to be flat within the range of elastic deformation and thereby easily opening the clip body on the side closer to the holding part 15. As the value of $\beta$ increases, the clip body can open wide on the side closer to the holding part 15 when the curved part 14 is deformed flat.

Figure 1F:
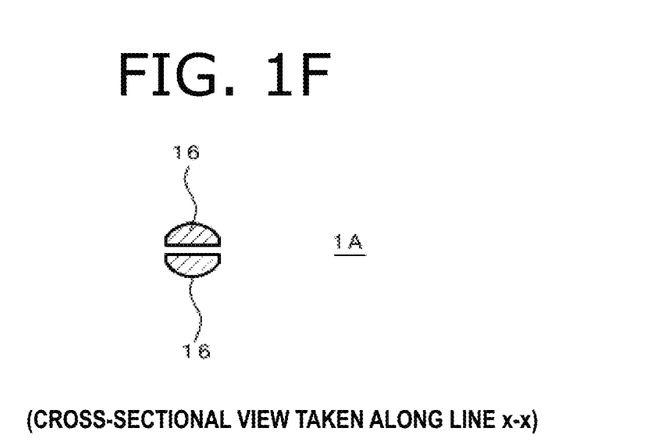
FIG. 1F is a cross-sectional view of the openable and closable clip according to the embodiment taken along line x-x.

The thickness of the intermediate part 16 is greater than that of the curved part 14. The intermediate part 16 includes a greater thickness part 17 in which a central region 16b of the intermediate part 16 toward the holding part 15 has a thickness L4 that is greater than a thickness L4' of a curved part-side region 16c closer to the curved part 14 than the central region 16b. As can be seen from a plan view (FIG. 1B) of the arm part 11, a width W1 of the arm part 11 in the central region 16b of the intermediate part 16 is greater than a width W2 of the arm part 11 in the curved part-side region 16c of the intermediate part 16, and the width of the arm part 11 is further increased in a holding part-side region 16a closer to the holding part 15 than the central region 16b. As just described, making the thickness of the entire intermediate part 16 greater than the thickness of the curved part 14 and providing the greater thickness part 17 having a large width and a large thickness in the central region 16b and the holding part-side region 16a of the intermediate part 16 makes it easier to impart stiffness to the arm part 11 which enables the holding parts 15 to be opened and then closed with an end P of the intermediate part 16 closer to the curved part serving as a fulcrum when the curvature of the curved part 14 is made flat. From the standpoint of enhancing such stiffness efficiently, the ratio L4/L3 between the thickness L4 of the greater thickness part 17 (the height of the arch shape) and the thickness L3 of the curved part 14 is preferably set to be greater than or equal to 2, more preferably 2 to 2.3 (FIG. 1C). From the same standpoint, the greater thickness part 17 preferably has a transverse section (cross-section perpendicular to the long-side direction of the arm part 11) of an arch shape, and has an approximately semicircular shape in the present embodiment (FIG. 1F). This can further enhance the stiffness of the arm part 11 that allows for the opening and closing operations of the clip body 10.

Moreover, making the thickness L4' of the curved part-side region 16c lesser than the thickness L4 of the central region 16b of the intermediate part 16 and making the width W2 of the curved part-side region 16c lesser than the width W1 of the central region 16b of the intermediate part 16 enables the fastening ring 2 to move onto the central region 16b instantly when the fastening ring 2 slides to the side closer to the intermediate part 16 from the side closer to the connecting part 12 than the curved part 14.

When the clip body 10 is closed, a region extending from the central portion of the intermediate part 16 to the curved part 14 forms a proximity region 18 where the pair of arm parts 11 are proximal to each other with a fixed distance therebetween. In the holding part-side region 16a on the side closer to the holding part 15 than the proximity region 18, the distance between the pair of arm parts 11 increases toward the holding part 15. A length L5 of the proximity region 18 is longer than a length Lr1 of the fastening ring 2 (FIG. 1C). When the clip body 10 is closed, a distance L6 between the outer surfaces of the pair of arm parts in the central region 16b of the intermediate part 16 is equal to the width W1 of the central region 16b as well as the inner diameter L2 of the fastening ring 2. This enables the fastening ring 2 to be positioned stably in the central region 16b of the intermediate part 16 after the object to be clipped is held.

The holding parts 15 of the pair of arm parts are brought into contact with each other or are located on closest positions when the openable and closable clip 1A is closed. The closest positions as used herein refer to the pair of holding parts 15 being positioned closest to each other during the course of the opening and closing operations of the openable and closable clip.

The opposing surfaces of the pair of holding parts 15 are provided with protrusions 19 to be meshed with one another when the clip body 10 is closed in order to prevent the object to be clipped that is held by the holding parts 15 from being displaced. In the present invention, the protrusions 19 are provided in accordance with the intended use of the openable and closable clip.

The holding part 15 is formed to have a large thickness as with the thickness of the greater thickness part 17 in the intermediate part 16. In view of this, consider a case where a fluorescent dye is contained in the resin that forms the clip body and such an openable and closable clip is used as a marker as will be described later. When such an openable and closable clip 1A is placed in the mucosa in the abdominal cavity and fluorescence emitted by the clip is observed from the serous membrane side, the large thickness of the holding part 15 increases the area of a distal end face 15a of the holding part 15 being pressed against the mucosa, thus yielding an advantage of increasing the fluorescence intensity to be observed. If the holding part 15 is formed to have a thickness similar to that of the curved part 14, in contrast, the area of the distal end face of the holding part becomes smaller, thus reducing the fluorescence intensity.

The fastening ring 2, on the other hand, has a tubular body with an inner diameter that is lesser than the maximum distance L1 between the outer surfaces of the curved parts 14 with the clip body 10 being closed and is equal to the distance L6 between the outer surfaces of the central regions 16b of the intermediate parts 16. By way of example, when the inner diameter of the outer sheath of the endoscope clip device is 2.1 mm, the length Lr1 of the fastening ring 2 in the axial direction of the tubular body is preferably set to 1.5 to 1.8 mm.

The clip body 10 including the above-described curved parts 14, intermediate parts 16, and holding parts 15 can be integrally molded by injection molding a resin. Thus, this openable and closable clip can be manufactured with high productivity and at a low cost.

Resin:

Polycarbonate, ABS, or the like, is preferably used as the resin that forms the clip body 10 so that high stiffness can be exhibited. The flexural modulus (JIS K 7171) of the resin is preferably greater than or equal to 2000 MPa, and the flexural strength (JIS K 7171) is preferably greater than or equal to 90 MPa.

Polycarbonate, ABS, or the like, is preferably used also from the standpoint of its excellent acid resistance and alkali resistance against digestive juices.

When the openable and closable clip is used as a marker, a fluorescent dye is preferably contained in the resin that forms the clip body 10. Fluorescent dyes that emit fluorescence in a wavelength region of red light to near infrared light from 600 to 1400 nm, preferably in a wavelength region of red light or near infrared light from 700 to 1100 nm, are preferably used as the fluorescent dye. Light in such a wavelength region has a high transmissive property to human tissues such as the skin, fat, and muscles. For example, such light can sufficiently reach the serous membrane surface from the mucosa of a tubular human tissue such as the rectum.

Examples of the fluorescent dyes that emit fluorescence in the above-described wavelength region may include riboflavin, thiamine, NADH (nicotinamide adenine dinucleotide), indocyanine green (ICG), an azo-boron complex compound described in Japanese Patent Application Laid-Open No. 2011-162445, and a dye having a condensed ring structure described in WO 2016/132596.

The preferable concentration of the fluorescent dye in the resin can be set depending on the kinds of the fluorescent dye and the resin, for example. Generally, the concentration is preferably set to 0.001 to 1% by mass.

As a method of incorporating the fluorescent dye into the resin, a biaxial kneader, for example, is used to knead the fluorescent dye into the resin. Thereafter, the clip body may be molded by injection molding.

A contrast medium such as radiopaque barium sulfate may be added to the resin as necessary. This enables the openable and closable clip 1A in the living body to be tracked by imaging the openable and closable clip 1A with X-rays even if the openable and closable clip 1A placed in the living body is accidentally detached. Also from the standpoint that the fluorescent dye is sensitized by barium sulfate, barium sulfate is preferably added.

For the resin that forms the fastening ring 2, on the other hand, no bending elasticity as in the resin that forms the clip body 10 is needed. The resin that forms the fastening ring 2 preferably has a high tensile strength. Polycarbonate, ABS, or the like, for example, can be used as such a resin.

Barium sulfate is preferably added also to the resin that forms the fastening ring 2 from the standpoint that the openable and closable clip 1A can be tracked when such a clip is accidentally detached in the living body.

Although the fastening ring 2 is made of a resin in the present embodiment, the fastening ring 2 may be made of a metal in the present invention. The reason why the fastening ring 2 may be made of a metal is as follows; if the openable and closable clip 1A is bitten by a stapler at the time of surgery, a place to be bitten would be practically somewhere in the clip body 10, and the possibility for the fastening ring 2 to be bitten is very little. This is because the fastening ring 2 is kept in the intermediate parts 16 provided between the curved parts 14 and the holding parts 15 with the openable and closable clip 1A holding a body tissue.

Figure 4A:
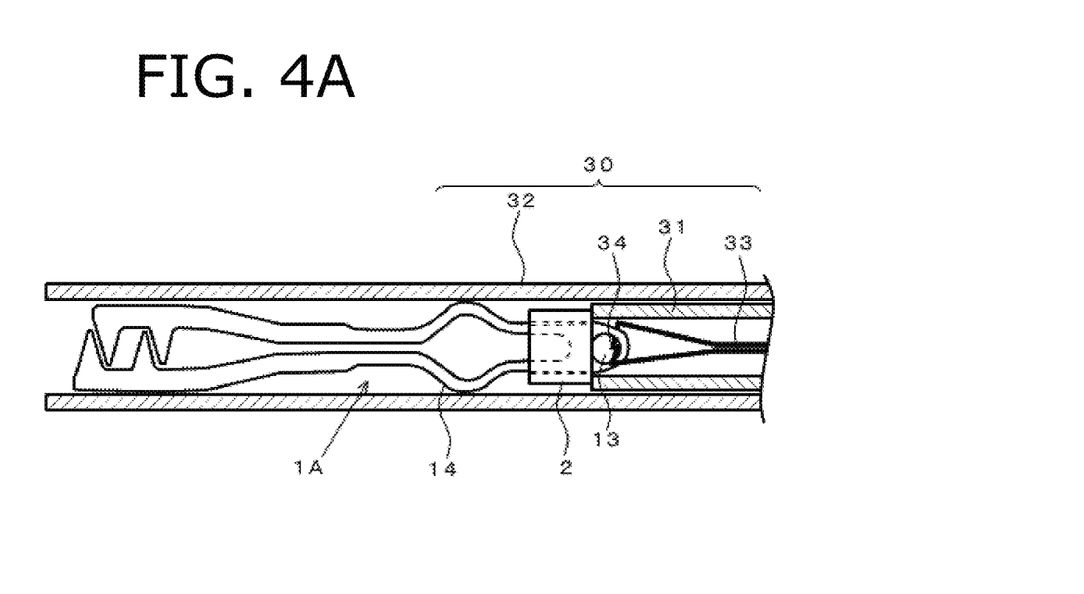
FIG. 4A is a cutaway cross-sectional view showing the openable and closable clip put into a clip sheath with the fastening ring being fitted onto the connecting part.

Method of Using Openable and Closable Clip:

As a method of using the openable and closable clip 1A as an endoscope clip, a clip sheath 30 for the endoscope clip device is used as shown in FIG. 4A, for example. A clip sheath including an inner sheath 31, an outer sheath 32, and a manipulation wire 33 described in Japanese Patent Nos. 4388324 and 5045484, or the like, can be used as the clip sheath 30. A commercially-available clip sheath can be employed as the clip sheath 30. The openable and closable clip 1A is inserted into the clip sheath 30 with the openable and closable clip 1A closed. A distal end hook 34 of the manipulation wire 33 is engaged with the hole 13 of the openable and closable clip 1A, and the inner sheath 31 is brought into contact with the fastening ring 2.

Figure 4B:
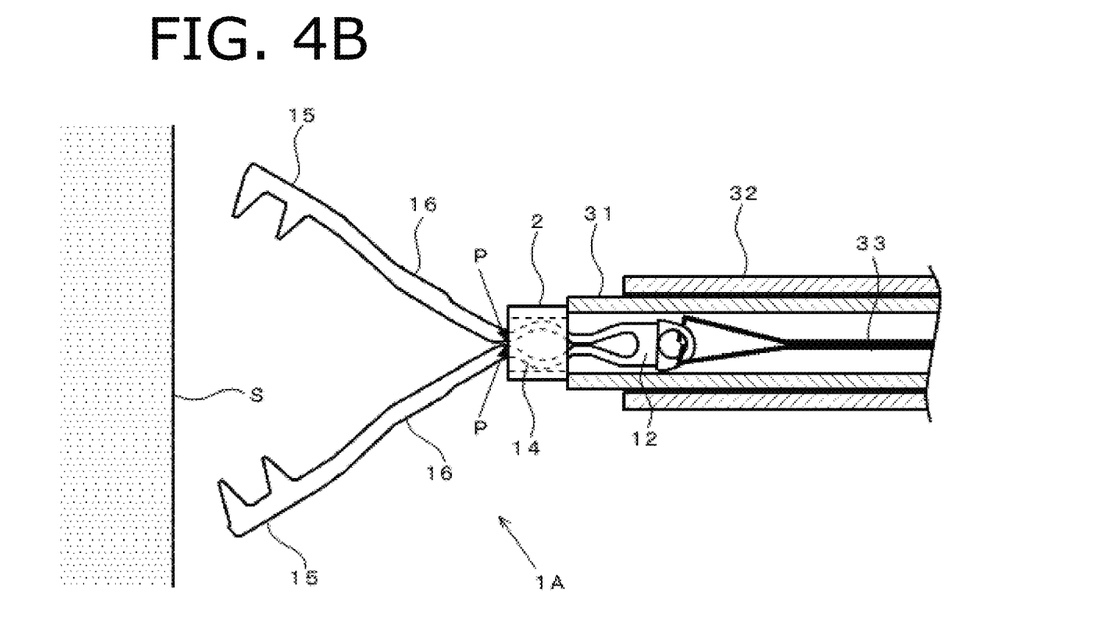
FIG. 4B is a cutaway cross-sectional view showing the openable and closable clip put into the clip sheath with the fastening ring sliding onto the curved parts.
Figure 4C:
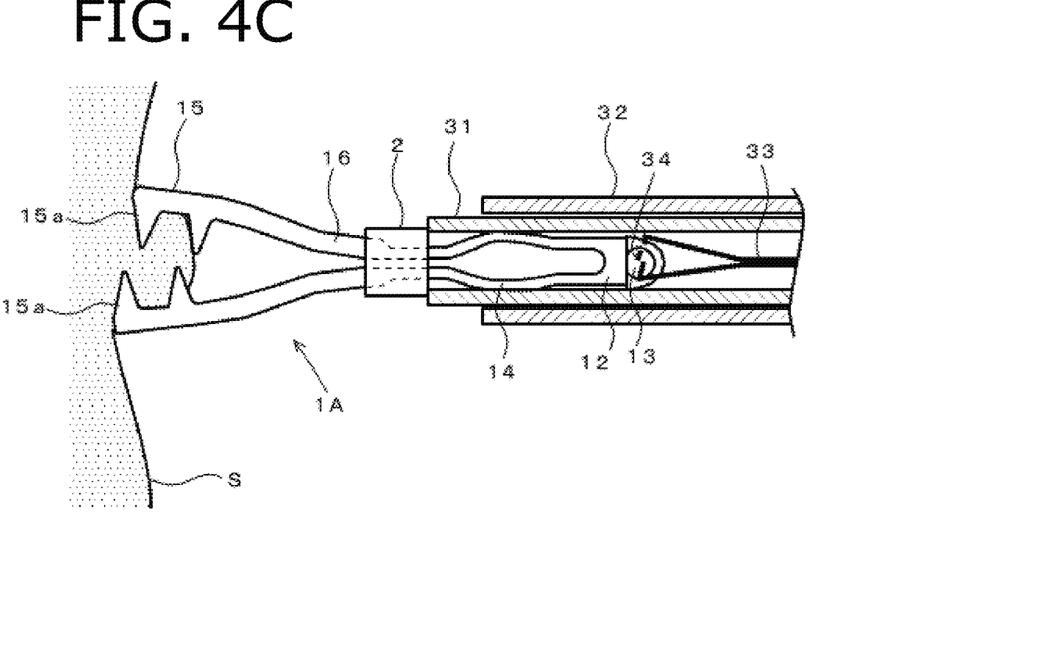
FIG. 4C is a cutaway cross-sectional view showing the openable and closable clip put into the clip sheath with the fastening ring sliding onto the intermediate part.
Figure 4D:
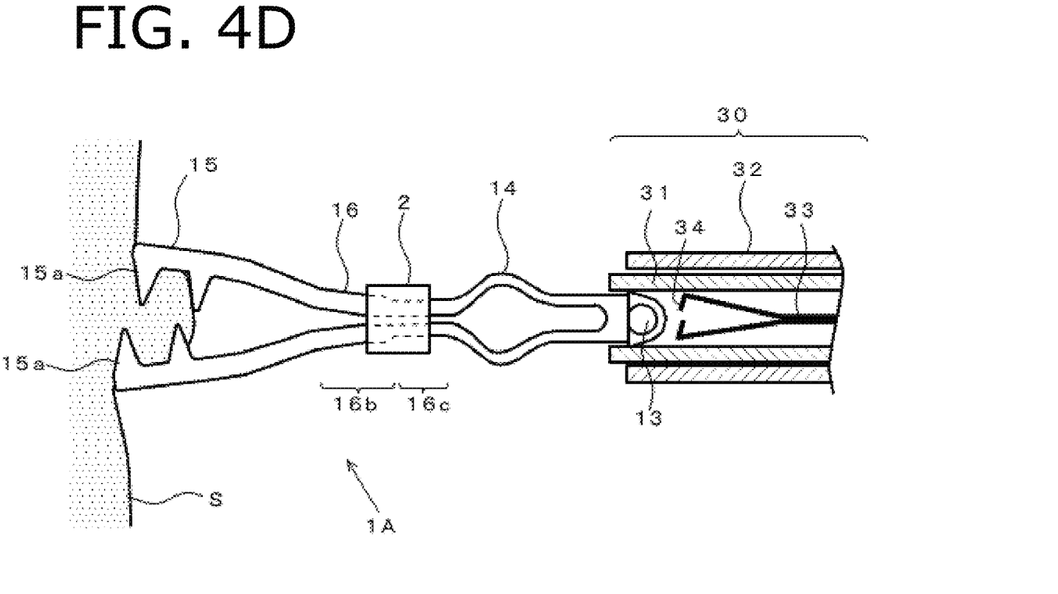
FIG. 4D is a cutaway cross-sectional view showing when the openable and closable clip put into the clip sheath comes off the clip sheath.

The clip sheath 30 is inserted into a hollow organ, for example, and the outer sheath 32 is moved so that a portion of the openable and closable clip 1A from the curved part 14 to the holding part 15 is exposed from the clip sheath 30. The fastening ring 2 is pushed in by the inner sheath 31 from the connecting part 12 side to the curved part 14 side, or the fastening ring 2 slides onto the curved parts 14 by pulling the manipulation wire 33. Consequently, as shown in FIG. 4B, the fastening ring 2 crushes the shape of the curved part 14 that is curved in a convex manner toward the outer side. With the end P of the intermediate part 16 closer to the curved part serving as a fulcrum, a portion from the end P to the holding part 15 pivots outwardly, thus opening the openable and closable clip 1A. The openable and closable clip 1A is moved to a site of mucosa S of the hollow organ to be marked, and the fastening ring 2 slides onto the intermediate parts 16 by the inner sheath 31. Consequently, the holding parts 15 are closed and the mucosa S is held by the holding parts 15 as shown in FIG. 4C. Subsequently, the inner sheath 31 is retracted. The engagement between the distal end hook 34 of the manipulation wire 33 and the hole 13 is released, and the openable and closable clip 1A is removed from the clip sheath 30. Consequently, the curved part 14 is returned to the shape before being crushed, and the closed shape of the openable and closable clip 1A is stabilized as shown in FIG. 4D. For the conventional clip in which a dogleg-shaped flat spring is closed by the fastening ring 2, force acts on the flat spring seeking to bring the closed state back to the state of the dogleg shape. For the openable and closable clip 1A, however, no such force is present when the openable and closable clip 1A is closed. Thus, the fastening ring 2 remains stable in the central region 16b or the curved part-side region 16c of the intermediate part 16, while the openable and closable clip 1A is placed in the hollow organ. This can eliminate an accident such as the openable and closable clip 1A holding the site to be marked before surgery being detached by the time the surgery is conducted.

Since the distal end face 15a of the holding part 15 having a greater thickness than the curved part 14 is in contact with the mucosa S with the openable and closable clip 1A holding the mucosa, the contact area between the distal end face 15a of the openable and closable clip 1A and the mucosa S is greater than that when the holding part 15 having a plate thickness similar to that of the curved part 14 is in contact with the mucosa. Thus, when the resin that forms the openable and closable clip 1A contains a fluorescent dye and the openable and closable clip 1A placed in the mucosa is irradiated with excitation light from the serous membrane side, the fluorescence can be observed from the serous membrane side at a high intensity level, and thus the position where the openable and closable clip 1A has been placed can be clearly identified.

Figure 5A:
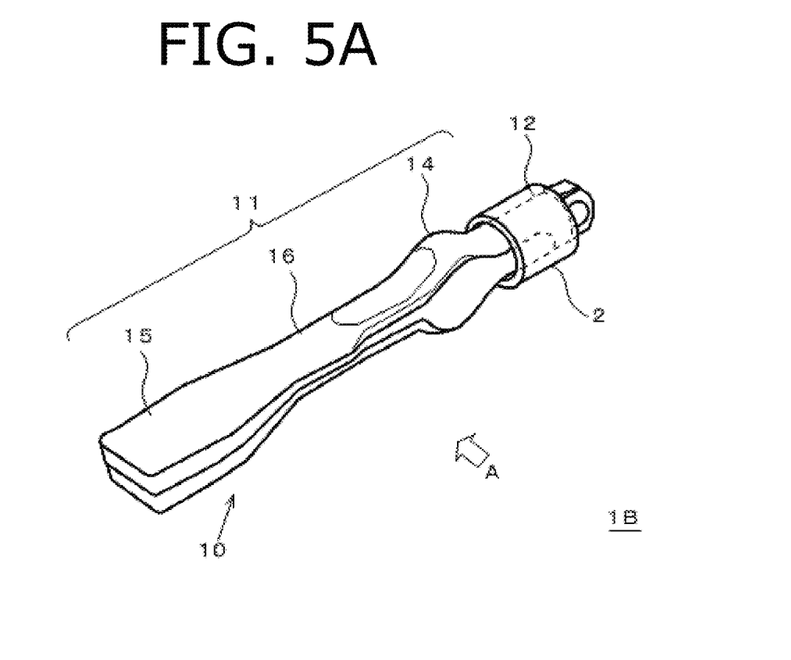
FIG. 5A is a perspective view showing an openable and closable clip according to another embodiment with a fastening ring being fitted onto a connecting part of a clip body.
Figure 5B:
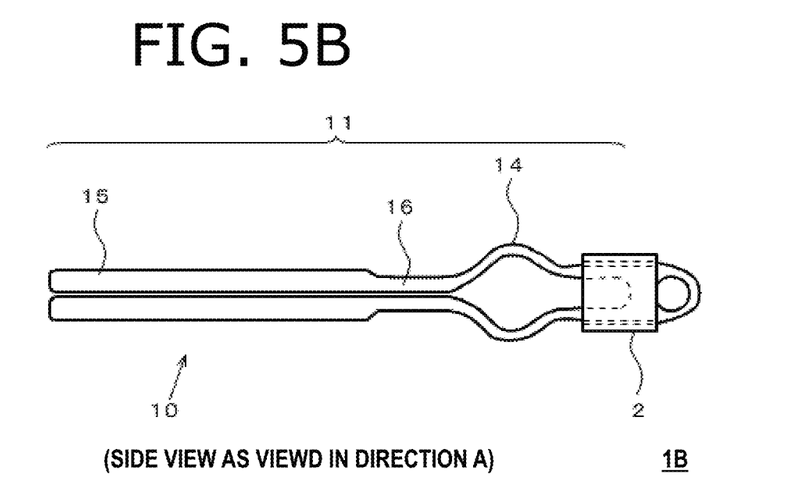
FIG. 5B is a side view showing the openable and closable clip according to the other embodiment with the fastening ring being fitted onto the connecting part of the clip body.

Modifications:

The openable and closable clip of the present invention can have various aspects. For example, when the clip is used as an aneurysm clip or a hemostatic clip, no protrusions 19 are preferably provided to the holding parts 15, and the opposing surfaces of intermediate parts 16 and the holding parts 15 are preferably made flat as in an openable and closable clip 1B shown in FIGS. 5A and 5B. When the clip is used as an aneurysm clip or a hemostatic clip, the inclusion of fluorescent dye in a clip body is unnecessary.

EXAMPLE

The present invention will be specifically described below with reference to an experimental example.

Figure 6A:
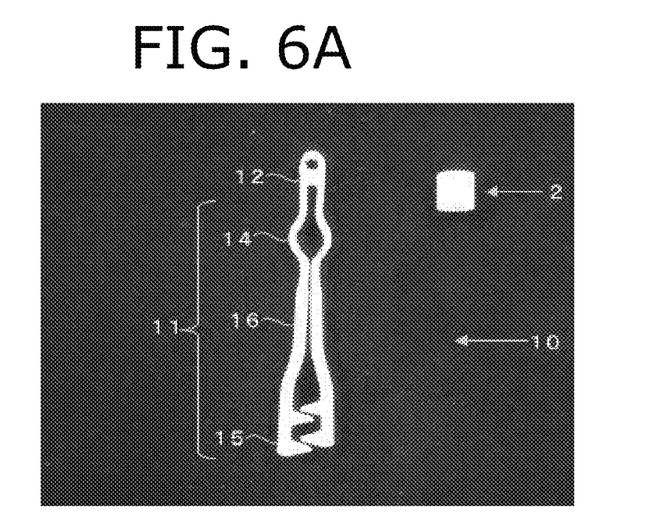
FIG. 6A is an exploded perspective view (photograph substituting for drawing) showing an openable and closable clip produced as an experimental example.

A clip body and a fastening ring of an openable and closable clip having the shape shown in FIG. 1A were produced with a resin. The photographs of those are shown in FIG. 6A.

Figure 6B:
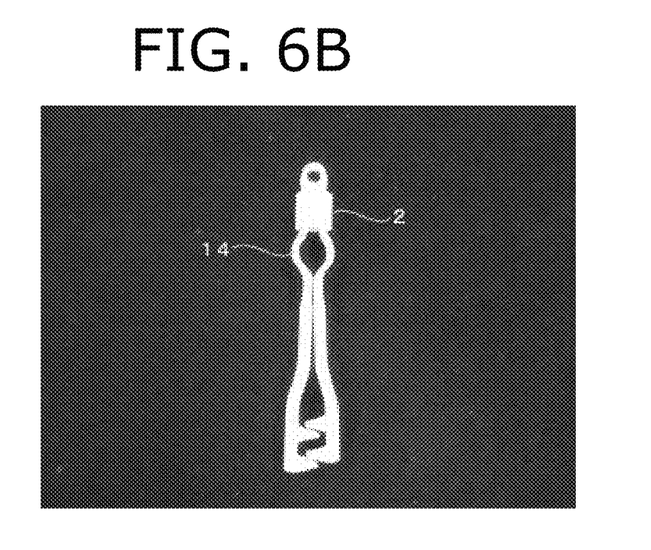
FIG. 6B is a perspective view (photograph substituting for drawing) showing the openable and closable clip produced as the experimental example in a closed state.
Figure 6C:
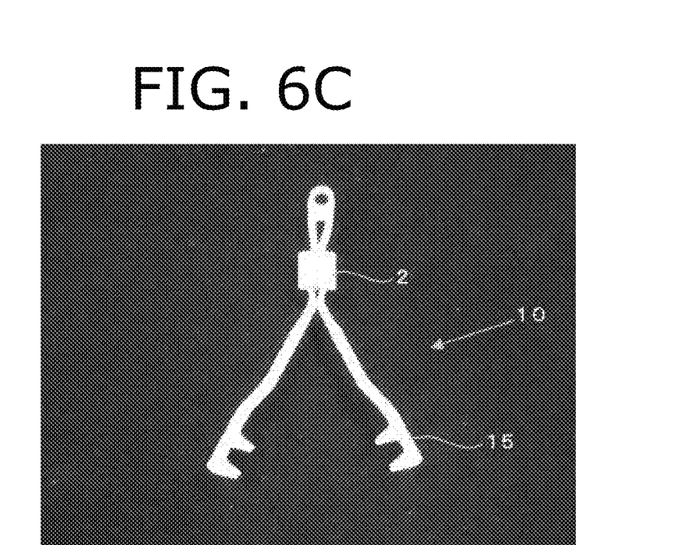
FIG. 6C is a perspective view (photograph substituting for drawing) showing the openable and closable clip produced as the experimental example in an opened state.
Figure 6D:
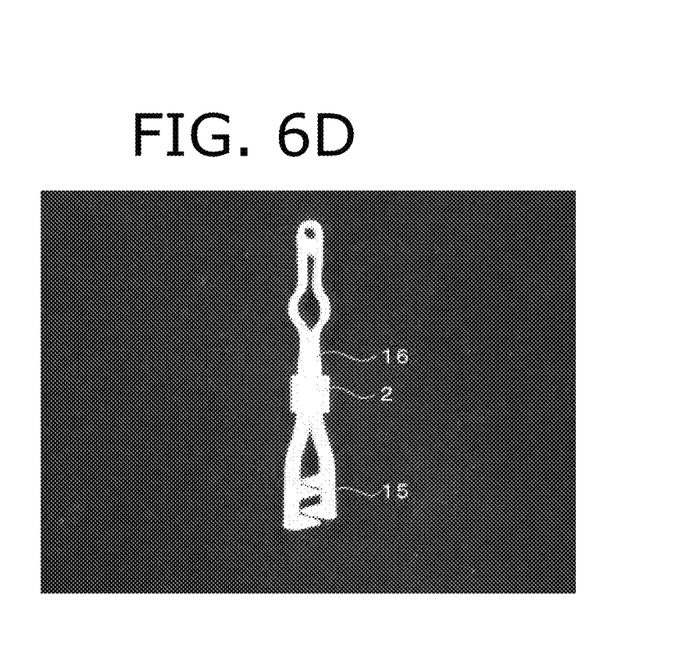
FIG. 6D is a perspective view (photograph substituting for drawing) showing the openable and closable clip produced as the experimental example in a closed state after having undergone the opened state.

The fastening ring 2 was fitted onto a connecting part 12 of the clip body 10 (FIG. 6B). When the fastening ring 2 was caused to slide onto curved parts 14, the clip body 10 was opened (FIG. 6C). When the fastening ring 2 was caused to further slide onto intermediate parts 16, the clip body 10 was closed (FIG. 6D). It was thus confirmed that the resin clip can be opened and closed by the sliding of the fastening ring 2.

REFERENCE SIGNS LIST

1A, 1B openable and closable clip
2 fastening ring
10 clip body
11 arm part
12 connecting part
13 hole
14 curved part
15 holding part
15a distal end face of holding part
16 intermediate part
16a holding part-side region
16b central region
16c curved part-side region
17 greater thickness part
18 proximity region
19 protrusion
30 clip sheath
31 inner sheath
32 outer sheath
33 manipulation wire
34 distal end hook
L1 maximum distance between outer surfaces of pair of curved parts
L2 inner diameter of fastening ring
L3 thickness of curved part
L4 thickness of greater thickness part (height of arch shape)
L4' thickness of curved part-side region of intermediate part
L5 length of proximity region
L6 distance between outer surfaces of pair of central portions of intermediate part
Lr1 length of fastening ring
P end of intermediate part closer to curved part
S mucosa
W1 width of arm part in greater thickness part
W2 width of arm part on side closer to curved part than greater thickness part

The invention claimed is:

1. An openable and closable clip for medical use, comprising a clip body made of a resin, and a fastening ring to be fitted onto the clip body, wherein
the clip body includes a pair of opposing arm parts, and a connecting part that connects base ends of the respective arm parts,
each of the arm parts includes a curved part on a base end side, a holding part on a distal end side, and an intermediate part between the curved part and the holding part,
the curved part is curved in an arc shape so that the pair of arm parts are away from each other,
the intermediate part has a thickness greater than that of the curved part, and
configuring an inner diameter of the fastening ring to be greater than a maximum diameter of the connecting part, lesser than a maximum distance between outer surfaces of the pair of curved parts in a closed state of the clip body, and greater than a distance between outer surfaces of curved part-side regions of the pair of intermediate parts in the closed state of the clip body enables the clip body to close when the fastening ring is removed from the clip body and when the fastening ring is fitted onto the clip body on a side closer to the connecting part than the curved part, open when the fastening ring slides onto the curved part from the connecting part, and close when the fastening ring slides onto the intermediate part from the curved part.

2. The openable and closable clip according to claim 1, wherein a greater thickness part is formed in a region ranging from a central portion of the intermediate part to a side closer to the holding part and has a thickness greater than that of the intermediate part on a side closer to the curved part.

3. The openable and closable clip according to claim 2, wherein the greater thickness part has a transverse section of an arch shape.

4. The openable and closable clip according to claim 1, wherein the clip body is integrally molded.

5. The openable and closable clip according to claim 1, wherein a fluorescent dye is contained in the resin that forms the clip body.

6. The openable and closable clip according to claim 1, wherein the fastening ring is made of a resin.

\* \* \* \* \*